United States Patent [19]

van der Meijden et al.

[11] 4,443,640

[45] Apr. 17, 1984

[54] PROCESS FOR THE PREPARATION OF AN AROMATIC HYDROCARBON MIXTURE

[75] Inventors: Johannes van der Meijden; Auke F. de Vries, both of Amsterdam, Netherlands

[73] Assignee: Shell Oil Company, Houston, Tex.

[21] Appl. No.: 375,850

[22] Filed: May 7, 1982

[30] Foreign Application Priority Data

May 20, 1981 [NL] Netherlands ........................ 8102470

[51] Int. Cl.³ .......................... C07C 2/52; C07C 12/46
[52] U.S. Cl. ..................................... 585/418; 208/137
[58] Field of Search ........................ 208/137; 585/418

[56] References Cited

U.S. PATENT DOCUMENTS 4,208,305 6/1980 Kouwenhoven et al. .......... 423/326

FOREIGN PATENT DOCUMENTS 21475 1/1981 European Pat. Off. .

Primary Examiner—Curtis R. Davis
Attorney, Agent, or Firm—Ronald R. Reper

[57] ABSTRACT

A process is disclosed for the preparation of aromatic hydrocarbon mixtures having high benzene content by contacting non-aromatic organic compounds with certain crystalline non-aluminum silicates having a $SiO_2/Fe_2O_3$ molar ratio of 100–300 and a $SiO_2/Al_2O_3$ molar ratio of 135–1900.

10 Claims, No Drawings

PROCESS FOR THE PREPARATION OF AN AROMATIC HYDROCARBON MIXTURE

BACKGROUND OF THE INVENTION

The invention relates to a process for the preparation of an aromatic hydrocarbon mixture having a high benzene content from non-aromatic organic compounds.

Benzene is an important base material in the chemical industry for, inter alia, the preparation of styrene via alkylation with ethene and dehydrogenation of the ethyl-benzene produced. An important source for the production of benzene is the hydrocarbon fraction boiling in the gasoline range which is obtained as a by-product in the preparation of ethene by thermal cracking of hydrocarbon oils, such as naphtha and gas oil. This hydrocarbon fraction, generally referred to as pyrolysis gasoline, has a very high benzene content. Extraction of the pyrolysis gasoline with a selective solvent for aromatics, such as sulfolane or diethylene glycol, yields an aromatic extract which, in addition to benzene, contains, inter alia, toluene and xylenes. Benzene may be isolated from this extract by distillation. The maximum quantity of benzene that can be produced in this way is dependent on the quantity of pyrolysis gasoline available, and thus on the demand for ethene. A group demand for benzene and an unchanged demand for ethene may give rise to problems in the supply of benzene. Since in the preparation of ethene by thermal cracking of hydrocarbon oils, not only aromatic by-products but, also, considerable quantities of non-aromatic by-products are formed, the applicants have carried out an investigation into the possibility of preparing benzene in an economically justified way by catalytic conversion of the latter by-products of ethene preparation. One of the motives for carrying out the investigation was the fact that new crystalline metal silicates having a special structure have recently been synthesized, which silicates show a high catalytic activity in the conversion of non-aromatic organic compounds into aromatic hydrocarbons, as described, for example, in U.S. Pat. Nos. 3,843,740, 3,843,741, 4,097,367, 4,238,318 and U.K. Pat. No. 1,555,928.

It has been found that if these silicates are used as the catalyst, an aromatic hydrocarbon mixture is obtained in which the aromatics substantially contain fewer than 12 carbon atoms, irrespective of the number of carbon atoms present in the organic compound used as the feed. The crystalline metal silicates concerned are characterized in that after one hour's calcination in air at 500° C. they have the following properties:

(a) thermally stable up to a temperature of at least 600° C., (b) an X-ray powder diffraction pattern in which the strongest lines are the four lines listed in Table 1:

TABLE 1

| d(Å) | Relative Intensity |
|---|---|
| 11.1 ± 0.2 | Very Strong |
| 10.0 ± 0.2 | Very Strong |
| 3.84 ± 0.07 | Strong |
| 3.72 ± 0.06 | Strong |

(c) in the formula which represents the composition of the silicate, expressed in moles of the oxides, and which, in addition to $SiO_2$, comprises either $Al_2O_3$ or $Fe_2O_3$, the $SiO_2/Al_2O_3$ and $SiO_2/Fe_2O_3$ molar ratios are higher than 10.

In the present patent application a crystalline silicate having a thermal stability of at least t° C. should be taken to be a silicate whose X-ray powder diffraction pattern remains substantially unchanged upon heating to a temperature of t° C.

The investigation carried out by applicants has shown that conversion of non-aromatic organic compounds over the aforementioned crystalline iron or aluminum silicates as catalysts does result in a hydrocarbon mixture having a high content of aromatic hydrocarbons of fewer than 12 carbon atoms in the molecule, but that these aromatic hydrocarbon mixtures comprise but little benzene.

Continued research carried out by the applicants has shown, however, that if the crystalline metal silicates having the special structure of the iron or aluminum silicates mentioned before, when used as catalysts for the conversion of non-aromatic organic compounds into an aromatic hydrocarbon mixture, contain both iron and aluminum and when, moreover, these metals are present in the silicates in such proportions that in the formula which represents the composition of the silicate, expressed in moles of the oxides, the $SiO_2/Fe_2O_3$ molar ratio is 100–300 and the $SiO_2/Al_2O_3$ molar ratio is 135–1900, result in an aromatic mixture with enhanced benzene content. This discovery is regarded as highly surprising in view of the disappointing results with respect to the production of benzene when using closely related crystalline metal silicates containing either only iron or only aluminum as the trivalent metal.

Summary of the Invention

The present patent application, therefore, relates to a process for the preparation of an aromatic hydrocarbon mixture having enhanced benzene content, which process comprises contacting a feed comprising one or more non-aromatic organic compounds with a crystalline metal silicate, which, after one hour's calcination in air at 500° C., has the properties mentioned above under (a) and (b) and which has the property that in the formula which represents the composition of the silicate expressed in moles of the oxides and which, in addition to $SiO_2$, comprises both $Fe_2O_3$ and $Al_2O_3$, the $SiO_2/Fe_2O_3$ molar ratio is in the range of 100–300 and the $SiO_2/Al_2O_3$ molar ratio is in the range of 135–1900.

Description of the Preferred Embodiments

In the process according to the invention, the starting material is a feed comprising one or more non-aromatic compounds. In addition to these, the feed may comprise one or more aromatic hydrocarbons. Preferably, a feed comprising more than 20% w of non-aromatic organic compounds is used. Examples of suitable non-aromatic compounds which, in the process according to the invention, can be converted into an aromatic hydrocarbon mixture having a high benzene content are oxygen-containing organic compounds, such as methanol and dimethyl ether, unbranched paraffins, such as propane, butane and pentane, branched paraffins, such as isobutane and isopentane, mono-olefins, such as propene and butene and diolefins, such as butadiene and pentadiene. The feed that is preferably used in the process according to the invention is a hydrocarbon mixture in which the hydrocarbons contain at least three carbon atoms and which hydrocarbon mixture substantially boils below 250° C. Special preference is given to such hydrocarbon mixtures in which the hydrocarbons contain at least four carbon atoms and which hydrocarbon mixtures substantially boil below 225° C. Examples of such hydrocarbon mixtures are gasoline fractions such as those obtained in the straight distillation of crude mineral oil and in catalytic and thermal cracking of mineral oil fractions. The feed preferably used as the starting material in the process according to the invention is a hydrocarbon fraction obtained as a by-product in the preparation of ethylene and/or propene by thermal cracking of hydrocarbons. This thermal cracking, which, as a rule, is carried out in the presence of steam and for which the starting materials may be light hydrocarbons, such as ethane, propane, or butane, or heavier hydrocarbons or hydrocarbon mixtures, such as naphtha, kerosine and gas oil, yields, besides the desired lower olefins, a considerable quantity of by-products, such as $C_4$ fraction, referred to as BBB, and a $C_5^+$ fraction boiling in the gasoline range which, as was already noted hereinbefore, is referred to as pyrolysis gasoline. As a rule, BBB consists substantially of butenes and butadiene and contains only a small quantity of butanes. A typical example of a BBB contains about 90% w of butenes and butadiene in about equal quantities by weight and about 10% w of butanes. Pyrolysis gasoline, as a rule, has a rather high concentration of mono- and diolefins and, moreover, a very high concentration of aromatics. A typical example of a pyrolysis gasoline contains about 20% w of $C_5$ mono- and diolefins in about equal quantities by weight, about 20% w of benzene and about 50% w of $C_7^+$ aromatics.

As examples of hydrocarbon mixtures obtained as by-products in the preparation of ethene and/or propene by thermal cracking of hydrocarbons, which hydrocarbon mixtures are suitable for use as starting material in the process according to the invention may be mentioned:

(a) the $C_4$ fraction (BBB)
(b) the $C_4$ fraction, after separation of at least part of the butadiene (after complete separation of butadiene the remaining part is referred to as BB)
(c) the pyrolysis gasoline
(d) the $C_5$ fraction of the pyrolysis gasoline
(e) the $C_5$ fraction of the pyrolysis gasoline after separation of at least part of the diolefins (isoprene, cyclopentadiene and dicyclopentadiene)
(f) the $C_6^+$ fraction of the pyrolysis gasoline
(g) the pyrolysis gasoline or its $C_6^+$ fraction after separation of at least part of the aromatics (for instance, the benzene/toluene/xylene fraction)
(h) mixtures of one of the fractions mentioned under (a) and (b) with one of the fractions mentioned under (c)–(g).

In the process according to the invention, special preference is given to the use of a hydrocarbon fraction as mentioned under (d) or (e) as the feed.

In the overall formula of the crystalline metal silicates used in the process according to the invention, the $SiO_2/Fe_2O_3$ molar ratio should be 100–300 and the $SiO_2/Al_2O_3$ molar ratio 135–1900. Crystalline metal silicates having an overall formula where the $SiO_2/Fe_2O_3$ molar ratio is 120–250 and the $SiO_2/Al_2O_3$ molar ratio is 175–1500 are preferably used.

The crystalline metal silicates used as catalysts in the process according to the invention are defined, inter alia, by the X-ray powder diffraction pattern which they show after one hour's calcination in air at 500° C. In this pattern the strongest lines should be the four lines listed in Table 1. The complete X-ray powder diffraction pattern of a typical example of a crystalline metal silicate used in the process according to the invention is given in Table 2.

TABLE 2

| d(Å) | Relative Intensity | d(Å) | Relative Intensity |
|---|---|---|---|
| 11.1 | 100 | 3.84 (D) | 57 |
| 10.0 (D) | 70 | 3.70 (D) | 31 |
| 8.93 | 1 | 3.63 | 16 |
| 7.99 | 1 | 3.47 | 1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |
| 4.00 | 4 | | |

(D) = doublet.

As is known from U.S. Pat. No. 4,208,305, incorporated herein by reference, the crystalline metal silicates are prepared starting from an aqueous mixture comprising the following compounds: one or more compounds of an alkali metal or alkaline-earth metal (M), one or more compounds containing an organic cation (R) or from which such a cation is formed during the preparation of the silicate, one or more silicon compounds, one or more compounds containing iron in the trivalent form and one or more aluminum compounds. The preparation is carried out by maintaining the mixture at an elevated temperature until the silicate has formed and subsequently separating the silicate crystals from the mother liquor and washing, drying and calcining the crystals. In the aqueous mixture from which the silicates are prepared, the various compounds should be present in the following ratios, expressed in moles of the oxides:

$M_{2/n}O:SiO_2 = 0.01-0.35$,
$R_{2/q}O:SiO_2 = 0.01-0.4$,
$SiO_2:Fe_2O_3 = 100-900$
$SiO_2:Al_2O_3 = 135-3800$ and
$H_2O:SiO_2 = 5-65$ (n is the valency of M, and q is the valency of R).

In the preparation of the silicates the starting mixture is preferably a mixture in which M is present in a sodium compound and R in a tetrapropyl ammonium compound.

The silicates prepared as described hereinabove contain alkali metal and/or alkaline-earth metal ions. By suitable exchange methods they can be replaced by other cations, such as hydrogen ions or ammonium ions. The crystalline silicates used in the process according to the invention preferably have an alkali metal content of less than 0.05% w.

As a rule, when the silicates are used as catalysts, they should be available in the form of particles 0.5–5 mm in diameter. The method of preparation as described hereinbefore yields silicates in the form of a fine powder. The silicates may be shaped to form particles of a larger size, for instance, by pressing. During shaping, the silicates may be combined with a binder material, such as kaolin or bentonite.

The process according to the invention can very suitably be carried out by passing the feed upwards or downwards through a vertically arranged reactor containing a fixed or moving bed of the crystalline metal silicates. Suitable conditions for carrying out the process according to the invention are a temperature of from 300°–650° C., a pressure of from 1–50 bar and a space velocity of from 0.1–10 g.g$^{-1}$.h$^{-1}$. The process is preferably carried out under the following conditions: a temperature of 425°–600° C., a pressure of 2.5–25 bar and a space velocity of 0.5–5 g.g$^{-1}$.h$^{-1}$.

When in the process according to the invention a feed containing 5 or more carbon atoms per molecule is used, a $C_4$ and lighter ($C_4{}^-$) fraction is obtained as a by-product. This $C_4{}^-$ fraction is preferably recirculated.

The invention is now elucidated with the aid of the following Example.

Example

Nine crystalline silicates 1–9) were prepared by heating, in water, in an autoclave under autogeneous pressure for 24 hours at 150° C., mixtures of NaOH, $(C_3H_7)_4NOH$, amorphous silica containing 50 ppmw Al (for the preparation of silicate 1) or amorphous silica containing 300 ppmw Al (for the preparation of silicates 2–9) with either $Fe(NO_3)_3$ (for the preparation of silicate 1), or $Al(NO_3)_3$ (for the preparation of silicate 2), or both $Fe(NO_3)_3$ and $Al(NO_3)_3$ (for the preparation of silicates 3–9). Upon cooling of the reaction mixtures the silicates formed were filtered off, washed with water until the pH of the wash water was about 8 and dried for 2 hours at 120° C. After 1 hour's calcination in air at 500° C., silicates 1–9 had the following properties:
(a) thermally stable up to a temperature of at least 800° C.,
(b) an X-ray powder diffraction pattern substantially corresponding with that given in Table 2,
(c) a value for the $SiO_2/Fe_2O_3$ and $SiO_2/Al_2O_3$ molar ratios as given in Table 3.

TABLE 3

| Silicate No. | $SiO_2/Fe_3O_3$ | $SiO_2/Al_2O_3$ |
|---|---|---|
| 1 | 189 | 6800 |
| 2 | — | 598 |
| 3 | 152 | 489 |
| 4 | 83 | 669 |
| 5 | 160 | 80 |
| 6 | 410 | 512 |
| 7 | 133 | 292 |
| 8 | 223 | 268 |
| 9 | 135 | 1260 |

The molar composition of the aqueous mixtures from which silicates 1–9 are prepared may be rendered as follows:

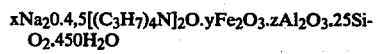

where x, y and z have the values listed in Table 4.

TABLE 4

| Silicate No. | x | y | z |
|---|---|---|---|
| 1 | 3 | 0.05 | 0.0006 |
| 2 | 1 | — | 0.033 |
| 3 | 3 | 0.07 | 0.025 |
| 4 | 3 | 0.16 | 0.020 |
| 5 | 3 | 0.063 | 0.25 |
| 6 | 3 | 0.02 | 0.025 |
| 7 | 1 | 0.0125 | 0.071 |
| 8 | 3 | 0.04 | 0.045 |
| 9 | 1 | 0.125 | 0.015 |

From silicates 1–9 were prepared silicates 16–18, respectively, by boiling silicates 1–9 with a 1.0 molar $NH_4NO_3$ solution, washing with water, boiling again with a 1.0 molar $NH_4NO_3$ solution and washing, drying at 120° C. and calcining at 500° C. In 16 experiments (Experiments 1–16) silicates 10–18 were tested as catalysts for the preparation of aromatic hydrocarbons starting from eight feedstocks (feedstocks A–H). The experiments were conducted in a 100 ml reactor containing a fixed catalyst bed of 20 ml volume. All the experiments were carried out at a space velocity of 1 g.g$^{-1}$.h$^{-1}$. In Experiments 1–11 the temperature was 550° C.; Experiments 13 and 15 were carried out at 500° C. and Experiments 12, 14 and 16 at 570° C. The pressure used in Experiments 1–12, 14 and 16 was 5 bar; Experiments 13 and 15 were carried out at 10 bar. The feeds used were:

Feed A $C_5{}^+$ pyrolysis gasoline, 99.7% w of which boiled below 220° C. and which has been obtained as a by-product in the preparation of ethene by thermal cracking of a naphtha/gas oil mixture in the presence of steam.

Feed B

A $C_5$ fraction separated from the $C_5{}^+$ pyrolysis gasoline used as Feed A.

Feed C

A $C_5$ fraction obtained after removal of isoprene, cyclopentadiene and dicyclopentadiene from the $C_5$ fraction used as Feed B.

Feed D $C_6{}^+$ pyrolysis gasoline obtained after the removal of the $C_5$ fraction and the $C_{6-8}$ aromatics from the $C_5{}^+$ pyrolysis gasoline used a Feed A.

Feed E

A pyrolysis gasoline from which benzene had been removed.

Feed F

BBB.

Feed G

N-Pentane.

Feed H

A naphtha fraction obtained by straight distillation of crude oil. The composition of the feeds used and the composition of the products after 30 hours have been recorded in Tables 5 and 6.

TABLE 5

(all experiments carried out using Feed A)

Product Composition, % w

| | Experiment No. | | | | | | | | | |
|---|---|---|---|---|---|---|---|---|---|---|
| | 1 | 2 | 3 | 4 | 5 | 6 | 7 | 8 | 9 | |
| | Silicate No. | | | | | | | | | Composition of |
| | 10 | 11 | 12 | 13 | 14 | 15 | 16 | 17 | 18 | Feed A, % w |
| $C_4^-$ | 6.9 | 6.3 | 8.6 | 5.5 | 7.9 | 8.2 | 8.1 | 9.9 | .7 | — |
| Benzene | 24.3 | 24.3 | 27.3 | 24.6 | 24.5 | 24.4 | 27.1 | 26.0 | 25.7 | 20.1 |
| $C_{7-12}$ Aromatics | 59.8 | 59.6 | 54.4 | 56.3 | 58.2 | 57.4 | 57.2 | 56.1 | 53.7 | |
| $C_{5-12}$ Non-aromatic Hydrocarbons | 4.6 | 1.9 | 3.5 | 4.9 | 3.1 | 4.1 | 0.3 | 2.6 | 1.2 | 25.9[a] |
| $C_{13}^+$ | 4.4 | 7.9 | 4.2 | 8.7 | 6.3 | 5.9 | 7.3 | 4.3 | 8.3 | 0.3 |
| Absolute increase in benzene content, % w | 4.2 | 4.2 | 7.2 | 4.5 | 4.4 | 4.3 | 7.0 | 5.9 | 5.6 | |
| Relative increase in benzene content, calculated on the increases in Experiments 1 and 2, % w | 0 | 0 | 71 | 7 | 5 | 2 | 67 | 40 | 33 | |

[a] $C_{5-12}$ paraffins = 2.8 gew. %; $C_{5-12}$ monoolefins = 10.6 gew. %; $C_{5-12}$ diolefins = 12.5 gew. %.

TABLE 6

(All experiments carried out using silicate 12)

| | Experiment No. | | | | | | |
|---|---|---|---|---|---|---|---|
| | 10 | 11 | 12 | 13 | 14 | 15 | 16 |
| | Feed | | | | | | |
| | B | C | D | E | F | G | H |
| | Composition of Feed (F) and of Product (P), % w | | | | | | | | | | | | | |
| | F | P | F | P | F | P | F | P | F | P | F | P | F | P |
| $C_4^-$ | 1.2 | 25.9 | 1.5 | 33.8 | 0.3 | 36.2 | — | 13.8 | 100[a] | 40.5 | — | 50.3 | — | 40.7 |
| Benzene | 0.3 | 7.4 | 1.5 | 7.4 | 6.5 | 10.6 | 1.3 | 11.7 | — | 13.9 | — | 7.4 | 1.7 | 7.9 |
| $C_{7-12}$ Aromatics | 1.8 | 51.9 | 1.8 | 44.9 | 8.0 | 37.0 | 59.9 | 67.3 | — | 42.0 | — | 30.9 | 6.8 | 40.0 |
| $C_{5-12}$ Non-Aromatic hydrocarbons | 96.7 | 11.6 | 96.4 | 11.6 | 85.2 | 14.7 | 38.8 | 5.3 | — | 1.0 | 100 | 10.2 | 91.5 | 10.3 |
| $C_{13}^+$ | — | 3.2 | — | 2.3 | — | 1.5 | — | 1.9 | — | 2.6 | — | 1.2 | — | 1.1 |

[a] Butanes = 9.4 gew. %; butenes = 46.8 gew. %; butadiene = 43.5 gew. %.

Of Experiments 1–9 mentioned in Table 5, only Experiments 3 and 7–9 are experiments according to the invention. In these experiments crystalline silicates were used having an $SiO_2/Fe_2O_3$ molar ratio between 100 and 300 and an $SiO_2/Al_2O_3$ molar ratio between 135 and 1900. In these experiments the relative increase in benzene content was from 33 to 71%, calculated on the increases in Experiments 1 and 2. Experiments 1, 2 and 4–6, listed in Table 5, are outside the scope of the invention; they have been included in the patent application for comparison. In Experiment 1 a silicate having an $SiO_2/Al_2O_3$ molar ratio of over 1900 was used; the silicate used in Experiment 2 contained no Fe; in Experiment 4 the $SiO_2/Fe_2O_3$ molar ratio of the silicate used was below 100; in Experiment 5 a silicate having an $SiO_2/Al_2O_3$ molar ratio below 135 was used; in Experiment 6 the $SiO_2/Fe_2O_3$ molar ratio of the silicate used was over 300. In Experiments 4–6 the relative increase in benzene content, calculated on the increases in Experiments 1 and 2, was only from 2 to 7%. All the experiments listed in Table 6 are experiments according to the invention.

We claim:

1. In a process for the preparation of an aromatic hydrocarbon mixture, which comprises contacting at a temperature in the range from about 300°–650° C., a pressure of from 1–50 bar, and a space velocity of from 0.1–10 g.g$^{-1}$.h$^{-1}$ a feed comprising one or more non-aromatic organic compounds with a crystalline metal silicate which, after one hour's calcination in air at 500° C., has the following properties:
   (a) thermally stable up to a temperature of at least 600° C.,
   (b) an X-ray powder diffraction pattern in which the strongest lines are the four lines listed in Table 1 of this specification;
the improvement comprising that said product shall have enhanced benzene content when in the formula which represents the composition of the silicate, expressed in moles of the oxides, and which, in addition to $SiO_2$, comprises both $Fe_2O_3$, and $Al_2O_3$, the $SiO_2/Fe_2O_3$ molar ratio is in the range of 100–300, and the $SiO_2/Al_2O_3$ molar ratio is in the range of 135–1900.

2. A process as in claim 1, wherein said feed comprises more than 20% w of non-aromatic organic compounds.

3. A process as in claim 1 or 2, wherein said feed is a hydrocarbon mixture in which the hydrocarbons contain at least three carbon atoms and in which a major portion of said hydrocarbon mixture boils below 250° C.

4. A process as in claim 3, characterized in that the feed is a hydrocarbon mixture in which the hydrocarbons contain at least four carbon atoms and in which a major portion of the hydrocarbon mixture boils below 225° C.

5. A process as in any one of claims 1–4, wherein said feed is a distillate hydrocarbon fraction obtained as a by-product in the preparation of ethene and/or propene by thermal cracking of hydrocarbons.

6. A process as in claim 5, wherein said feed is the $C_5$ fraction of a pyrolysis gasoline.

7. A process as in claim 5, wherein said feed is the $C_5$ fraction of a pyrolysis gasoline from which $C_5$ fraction at least part of the diolefins have been separated.

8. A process as in any one of claims 1–2, wherein in the overall formula of the crystalline metal silicate the $SiO_2/Fe_2O_3$ molar ratio is 120–250 and the $SiO_2/Al_2O_3$ molar ratio is 175–1500.

9. A process as in any one of claims 1–2, wherein the crystalline metal silicate has an alkali metal content of less than 0.05% w.

10. A process as in claim 9, carried out at a temperature of from 425°–600° C., a pressure of from 2.5–25 bar and a space velocity of from 0.5–5 g.g$^{-1}$h$^{-1}$.

* * * * *